United States Patent [19]
Sasamine et al.

[11] Patent Number: 5,701,911
[45] Date of Patent: Dec. 30, 1997

[54] GUIDE WIRE EXTENSION DOCKING SYSTEM

[75] Inventors: Kazuo Sasamine, Lemon Grove; Garry E. Rupp, Santee, both of Calif.

[73] Assignee: Medtronic, Inc., Minneapolis, Minn.

[21] Appl. No.: 628,880

[22] Filed: Apr. 5, 1996

[51] Int. Cl.$^6$ .................................................. A61B 5/00
[52] U.S. Cl. ............................................................ 128/772
[58] Field of Search ........................... 128/657, 658, 128/772; 604/280, 283

[56] References Cited

U.S. PATENT DOCUMENTS

| | | | |
|---|---|---|---|
| Re. 34,466 | 12/1993 | Taylor et al. | 128/657 |
| 4,917,103 | 4/1990 | Gambale et al. | 128/772 |
| 4,922,923 | 5/1990 | Gambale et al. | 128/772 |
| 5,031,636 | 7/1991 | Gambale et al. | 128/772 |
| 5,109,867 | 5/1992 | Twyford, Jr. | 128/772 |
| 5,113,872 | 5/1992 | Jahrmarkt et al. | 128/772 |
| 5,117,838 | 6/1992 | Palmer et al. | 128/772 |
| 5,188,621 | 2/1993 | Samson | 604/283 |
| 5,197,486 | 3/1993 | Frassica | 128/772 |
| 5,234,002 | 8/1993 | Chan | 128/772 |
| 5,271,415 | 12/1993 | Foerster et al. | 128/772 |
| 5,282,478 | 2/1994 | Fleischhaker et al. | 128/772 |
| 5,415,178 | 5/1995 | Hsi et al. | 128/772 |

*Primary Examiner*—Max Hindenburg
*Attorney, Agent, or Firm*—Michael R. Shevlin; Dianne M. F. Plunkett; Harold R. Patton

[57] ABSTRACT

A method and apparatus for a guide wire extension docking system for angioplasty including a guide wire and an extension wire to facilitate exchanging a balloon dilatation catheter comprising a guide wire having a proximal end and a distal end, an extension wire having a proximal end and a distal end, a hypotube having a proximal end, a distal end, an inner diameter and an outer diameter, the outer diameter of the hypotube being equal to the diameter of the extension wire, the proximal end of the hypotube being permanently affixed to the distal end of the extension wire, the distal end of the hypotube having a tongue extending distally and a spring coil with a proximal end, a distal end, an inner diameter and an outer diameter, the outer diameter of the spring coil being equal to the outer diameter of the hypotube, the spring coil having a length approximately twice the length of the tongue, the outer diameter of the spring coil being permanently affixed to the tongue such that the proximal end of the spring coil is adjacent to and axially aligned with the distal end of the hypotube, the inner diameter of the spring coil being dimensioned to slidably fit the proximal end of the guide wire with a frictional fit such that when the guide wire is inserted into the distal end of the spring coil, the guide wire is held in place by frictional engagement with the spring coil.

6 Claims, 2 Drawing Sheets

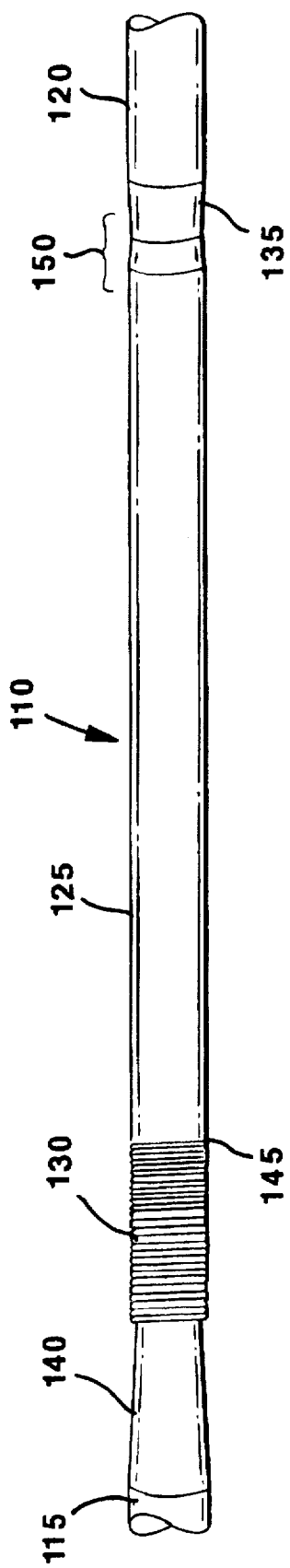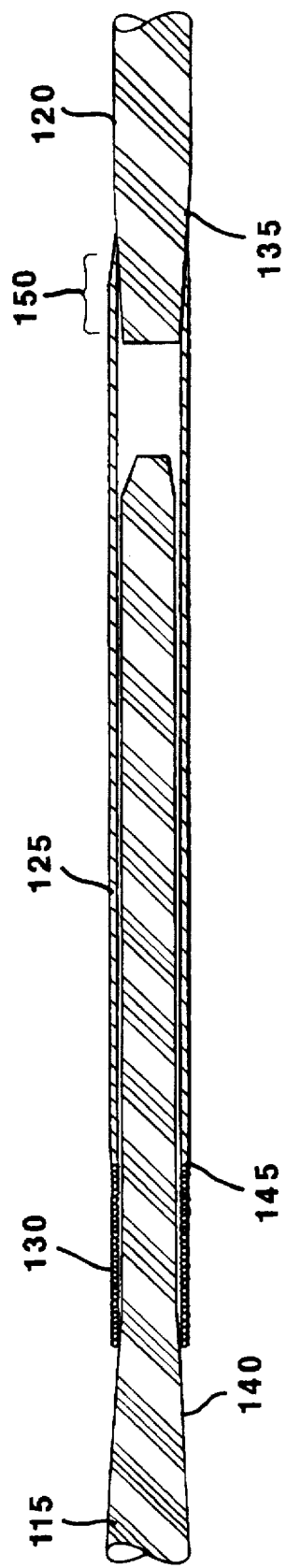

GUIDE WIRE EXTENSION DOCKING SYSTEM

FIELD OF THE INVENTION

This invention relates to guide wires used in angioplasty, and more particularly to the extension of the guide wire to facilitate the exchange of dilatation catheters.

BACKGROUND OF THE INVENTION

Percutaneous transluminal coronary angioplasty (PTCA) is used to reduce arterial build-up of cholesterol fats or atherosclerotic plaque. According to this procedure, a blockage in a coronary artery can be reduced by positioning a balloon dilatation catheter across the blockage and inflating the balloon, which causes stretching of the artery and pressing of the lesion into the artery wall to re-establish acceptable blood flow through the artery. The first marketable PCTA catheters for angioplasty were "fixed wire" catheters, in which a core or guide wire was fixed within the catheter to stiffen it so that it could be pushed into position in the vascular system. If a different catheter size was required, the fixed wire catheter had to be completely removed and a new one inserted. This is a tedious and time consuming process.

Subsequently an "over-the-wire" catheter was developed in which a guide wire was slidably placed within a lumen of the catheter. The guide wire lumen passed from the distal end of the catheter through the balloon to the proximal end of the catheter. This system provided reasonably easy placement of the catheter because the guide wire was inherently smaller and more flexible than the fixed wire system so one could more readily select the desired coronary artery and reach smaller branches. Once the guide wire was positioned beyond the stenosis, the catheter was then slid over the guide wire so that placement of the balloon spanned the stenosis and the balloon was then inflated. Once the catheter is inflated to dilate the stenosis, it is not uncommon for the physician to require use of a subsequent larger size of balloon to open the artery. There are different methods used to exchange the catheter and all of them have the same goal, to exchange the catheter without losing the position across the stenosis.

When performing the catheter exchange it is important to keep the guide wire in the same position so that the guide wire may be used to guide the next catheter to the stenosis. One method of exchange is to remove the initial guide wire and replace it with an exchange wire that is over double the length of the catheter. Once the exchange wire is in place, the catheter is slid over the exchange wire and the catheter is removed, then the next catheter is slid over the exchange wire to the stenosis.

Another method of exchanging the catheter is to use an extension wire. The extension wire is attached to the proximal end of the guide wire that is already in place. With the extension wire attached, the combination of the guide wire and extension wire is approximately the same length as an exchange wire. The advantage of this method is that the original guide wire that has already crossed the stenosis does not have to be disturbed during the catheter exchange.

There are different methods of attaching the extension wire to the guide wire. U.S. Pat. No. 4,917,103 to Gambale et al. describes a connection between the guide wire and extension wire that crimps the extension wire to the proximal end of the guide wire making a permanent connection. U.S. Pat. No. 5,197,486 to Frassica describes a connection where the proximal end of the guide wire has a reduced diameter male element that attaches to a female element at the distal end of the extension wire by using an interference fit. U.S. Pat. No. Re. 34,466 to Taylor et al. describes another male/female connection between the guide wire and the extension wire.

There are other methods that add intermediate parts between the guide wire and extension wire that connects them together (see U.S. Pat. No. 5,188,621 to Samson, U.S. Pat. No. 5,271,415 to Foerster et al., U.S. Pat. No. 5,234,002 to Chan, U.S. Pat. No. 4,922,923 to Gambale et al., U.S. Pat. No. 5,031,636 to Gambale et al., U.S. Pat. No. 5,133,872 to Jahrmarkt et. al. and U.S. Pat. No. 5,117,838 to Palmer et al.) or use retractable sleeves that enclose interlocking members of the guide wire and extension wire (see U.S. Pat. No. 5,109,867 to Twyford).

There are problems associated with the aforementioned connections. Connections that use male/female friction to hold the guide wires together may disconnect if any torsional forces are used during the exchange. Connections that use crimping devices require special equipment, may be somewhat awkward to use and are not readily disconnectable. Connections with intermediate parts cannot connect the guide wires if those parts are lost or misplaced during a procedure. Connections using retractable sleeves may jam or stick with foreign material and not allow the connection.

SUMMARY OF THE INVENTION

The object of the invention is to provide a new and improved guide wire extension docking system that cures the problems that have been encountered by prior extension systems. This is accomplished by making a connection between the guide wire and the extension wire that makes it simple to attach the wires together, can transfer torsional forces between the wires and can be readily disconnected/reconnected when required.

Accordingly, the present invention is directed to a guide wire extension docking system comprising a guide wire having a proximal end and a distal end, an extension wire having a proximal end and a distal end, a hypotube having a proximal end, a distal end, an inner diameter and an outer diameter, the outer diameter of the hypotube being equal to the diameter of the extension wire, the proximal end of the hypotube being permanently affixed to the distal end of the extension wire, the distal end of the hypotube having a tongue extending distally and a spring coil with a proximal end, a distal end, an inner diameter and an outer diameter, the outer diameter of the spring coil being equal to the outer diameter of the hypotube, the spring coil having a length approximately twice the length of the tongue, the outer diameter of the spring coil being permanently affixed to the tongue such that the proximal end of the spring coil is adjacent to and axially aligned with the distal end of the hypotube, the inner diameter of the spring coil being dimensioned to slidably fit the proximal end of the guide wire with a frictional fit such that when the guide wire is inserted into the distal end of the spring coil, the guide wire is held in place by frictional engagement with the spring coil.

BRIEF DESCRIPTION OF THE DRAWINGS

The foregoing and other features of the present invention will be best appreciated with reference to the following detailed description of a specific embodiment of the invention, when read in conjunction with the accompanying drawings.

FIG. 3 is a view showing an alternate configuration present invention assembled; and FIG. 4 is cross-sectional view of FIG. 3 showing the proximal end of the guide wire and the distal end of the extension wire with the alternate configuration of the connection features of the present invention.

DETAILED DESCRIPTION OF THE PREFERRED EMBODIMENTS

Figure 1:
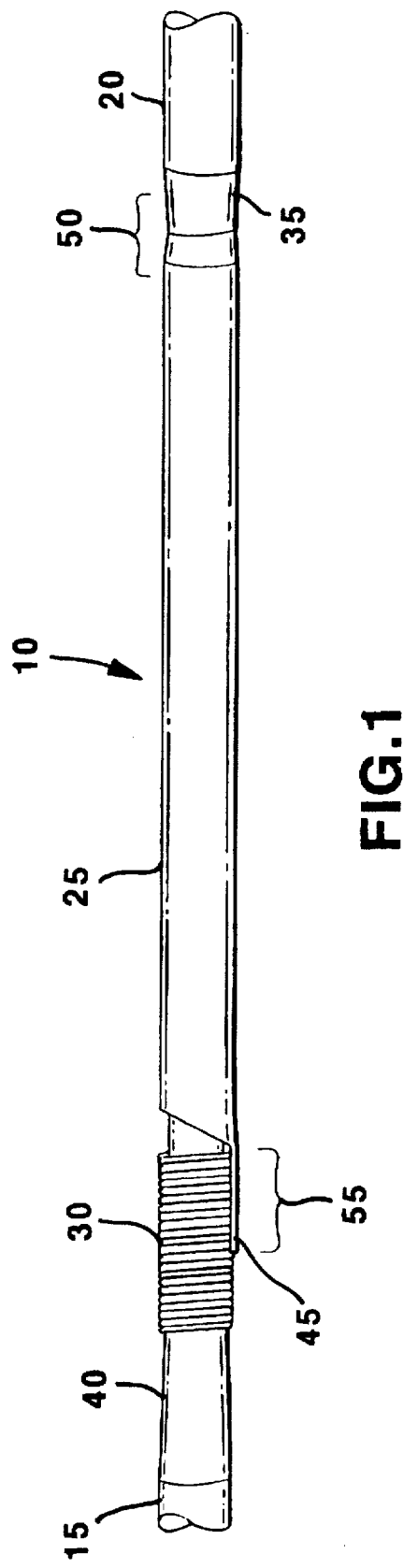
FIG. 1 is a view showing the present invention assembled.

The present invention is directed to a guide wire extension docking system 10 utilizing a spring coil connection between a guide wire 15 and an extension wire 20. The use of the guide wire extension docking system 10 avoids the need for a separate exchange length wire when exchanging a balloon dilatation catheter. At the distal end of the extension wire 20 is a hypotube 25 and a spring coil 30. When the proximal end 40 of the guide wire 15 is inserted into the spring coil 30, the guide wire 15 and the extension wire 20 create the guide wire extension docking system 10. The spring coil connection between the guide wire 15 and the extension wire 20 makes it simple to attach the wires together, transfers torsional forces between the wires and is readily disconnected/reconnected when required. While the following describes the hypotube 25 and the spring coil 30 being located on the distal end 35 of the extension wire 20, they could also be located on the proximal end 40 of the guide wire 15.

Figure 2:
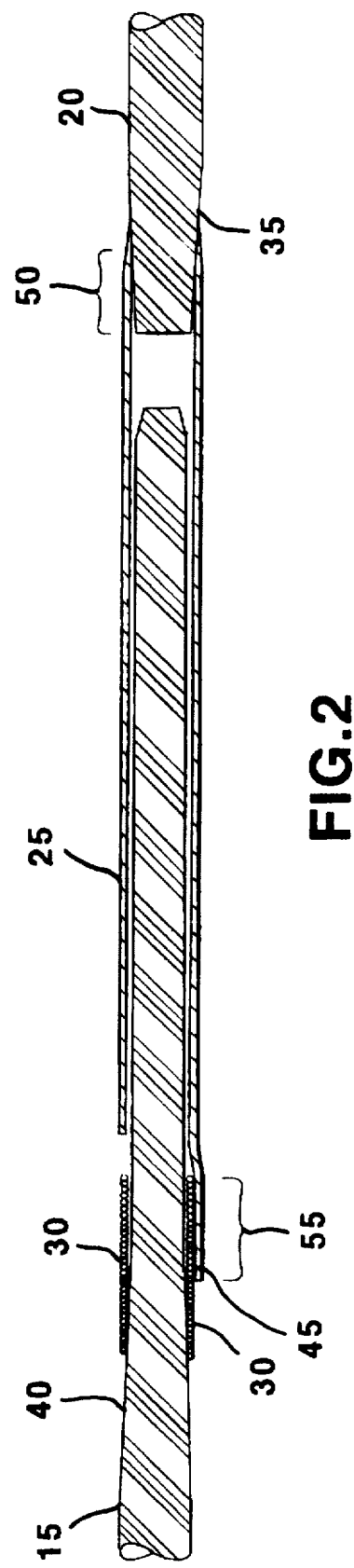
FIG. 2 is a cross-sectional view of FIG. 1 showing the proximal end of the guide wire and the distal end of the extension wire with the connection features of the present invention.

FIGS. 1 and 2 show the first embodiment of the present invention of the guide wire docking system 10. The guide wire docking system includes a guide wire 15 and an extension wire 20 with a hypotube 25 and a spring coil 30 at the distal end 35. The guide wire 15 is made of any guide wire construction modified at the proximal end 40 to have a taper that fits inside the spring coil 30. Standard guide wires for angioplasty are constructed of metal (stainless steel, nitinol, etc.) and have diameters ranging from 0.010" to 0.018". The exact construction of the guide wire 15 (other than the proximal end 40) is not critical to the invention and will not be described in any detail.

The hypotube 25 is a constant diameter tube made of stainless steel with a proximal end, a distal end, an inside diameter and an outside diameter. The outside diameter of the hypotube 25 is equal to the outside diameter of the extension wire 20. The extension wire 20 is generally formed from an elongated, constant diameter wire modified with a taper or step down diameter at the distal end 35 to fit the inside diameter of the proximal end of the hypotube 25. The distal end 35 of the extension wire 20 is inserted into the proximal end of the hypotube 25 and welded 50 in place. At the distal end of the hypotube 25 is a tongue 45. The tongue 45 has the same thickness as the hypotube 25 and can either be made as part of the hypotube 25 or made separately and welded to the distal end of the hypotube 25. The length of the tongue 45 is approximately one half the length of the spring coil 30. The spring coil 30 is made from stainless steel and has an inside diameter and an outside diameter. The outside diameter of the spring coil 30 has the same dimension as the outside diameter of the hypotube 25. The spring coil 30 is placed on the tongue 45 so that the proximal end of the spring coil 30 touches the distal end of the hypotube 25. Once the spring coil 30 and the hypotube 25 are coaxially aligned, the spring coil 30 is bonded 55 to the tongue 45.

FIGS. 3 and 4 show a second embodiment of the present invention of a guide wire extension docking system 110. The guide wire extension docking system 110 includes a guide wire 115 and an extension wire 120 with a hypotube 125 and a spring coil 130 at the distal end 135. The guide wire 115 is made of any guide wire construction modified at the proximal end 140 to have a taper that fits inside the spring coil 130. Standard guide wires for angioplasty are constructed of metal (stainless steel, national, etc.) And have diameters ranging from 0.010" to 0.018". The exact construction of the guide wire 115 (other than the proximal end 140) is not critical to the invention and will not be described in any detail.

The hypotube 125 is a constant diameter tube made of stainless steel with a proximal end, a distal end, an inside diameter and an outside diameter. The outside diameter of the hypotube 125 is equal to the outside diameter of the extension wire 120. The extension wire 120 is generally formed from an elongated, constant diameter wire modified with a taper or step down diameter at the distal end 135 to fit the inside diameter of proximal end of the hypotube 125. The distal end 135 of the extension wire 120 is inserted into the proximal end of the hypotube 125 and welded 150 in place. The spring coil 130 is made from stainless steel and has an inside diameter and an outside diameter. The outside diameter of the spring coil 130 has the same dimension as the outside diameter of the hypotube 125. The spring coil 130 is coaxially aligned and welded 145 to the proximal end of the hypotube 125.

The proximal end (40, 140) of the guide wire (15, 115) is adapted to be inserted into the distal end of the spring coil (30, 130) to engage and join the extension wire (20, 120) with the guide wire (15, 115). Once joined, the rotation of the extension wire (20, 120) causes rotation of the guide wire (15, 115) through the connection. The extension wire (20, 120) is sufficiently long so that when the guide wire (15, 115) and the extension wire (20, 120) are connected together, the combination has an overall length suitable for exchanging catheters without removing the guide wire (15, 115) from the patient's vascular system. The length of the guide wire (15, 115) is approximately 175–195 cm and the length of the extension wire (20, 120) is approximately 125 cm. The connection between the two wires provides a substantially continuous outer diameter between the guide wire (15, 115) and the extension wire (20, 120).

In use, the guide wire (15, 115) is introduced into the patient with a balloon dilatation catheter in the patient's femoral artery. The guide wire (15, 115) is advanced to the selected coronary artery and across the stenosis. Once in place, the guide wire (15, 115) is held in place as the balloon dilatation catheter is advanced along the guide wire (15, 115) until the inflatable balloon spans the stenosis. The balloon is then inflated to dilate the stenosis. While in the patient, the only part of the guide wire (15, 115) that is exposed is the proximal end (45, 145). To exchange the catheter, the balloon is deflated, the distal end (35, 135) of the extension wire (20, 120) with the hypotube (25, 125) and the spring coil (30, 130) is then attached to the proximal end (40, 140) of the guide wire (15, 115) for positive engagement. Once connected, the guide wire (15, 115) and the extension wire (20, 120) will act as one unit and may be twisted and rotated. While holding the extension wire (20, 120), the balloon catheter is removed by sliding it off over the extension wire (20, 120). The new catheter is then slid on over the extension wire (20, 120) and the guide wire (15, 115) until its balloon reaches the stenosis. The extension wire (20, 120) may then be disengaged from the guide wire (15, 115).

The preceding specific embodiments are illustrative of the practice of the invention. It is to be understood, however, that other expedients known to those skilled in the art or disclosed herein, may be employed without departing from the spirit of the invention or the scope of the appended claims.

| No. | Component |
|---|---|
| 10 | Guide Wire Extension Docking System |
| 15 | Guide Wire |
| 20 | Extension Wire |
| 25 | Hypotube |
| 30 | Spring coil |
| 35 | Extension Wire - Distal End |
| 40 | Guide Wire - Proximal End |
| 45 | Tongue |
| 50 | Weld - Hypotube to Extension Wire |
| 55 | Bond - Spring coil to Tongue |
| 110 | Guide Wire Docking System |
| 115 | Guide Wire |
| 120 | Extension Wire |
| 125 | Hypotube |
| 130 | Spring coil |
| 135 | Extension Wire - Distal End |
| 140 | Guide Wire - Proximal End |
| 145 | Weld - Spring coil to Hypotube |
| 150 | Weld - Hypotube to Extension Wire |

What is claimed is:

1. A guide wire extension docking system for angioplasty including a guide wire and an extension wire to facilitate exchanging a balloon dilatation catheter comprising:
   (a) a guide wire having a proximal end with a first diameter and a distal end with a second diameter;
   (b) an extension wire having a proximal end with a first diameter and a distal end with a second diameter, the first diameter of the extension wire being equal to the second diameter of the guide wire;
   (c) a hypotube having a proximal end, a distal end, an inner diameter and an outer diameter, the outer diameter of the hypotube being equal to the first diameter of the extension wire, the proximal end of the hypotube being permanently affixed to the distal end of the extension wire, the distal end of the hypotube having a tongue extending distally; and
   (d) a spring coil with a proximal end, a distal end, an inner diameter and an outer diameter, the outer diameter of the spring coil being equal to the outer diameter of the hypotube, the spring coil having a length approximately twice the length of the tongue, the outer diameter of the spring coil being permanently affixed to the tongue such that the proximal end of the spring coil is adjacent to and axially aligned with the distal end of the hypotube, the inner diameter of the spring coil being dimensioned to slidably fit the first diameter of the guide wire with a frictional fit such that when the first diameter of the guide wire is inserted into the distal end of the spring coil, the guide wire is held in place by frictional engagement with the spring coil.

2. The guide wire extension docking system of claim 1 wherein the guide wire, extension wire, hypotube and spring coil are made of stainless steel.

3. A guide wire extension docking system for angioplasty including a guide wire and an extension wire to facilitate exchanging a balloon dilatation catheter comprising:
   (a) a guide wire having a proximal end with a first diameter and a distal end with a second diameter;
   (b) an extension wire having a proximal end with a first diameter and a distal end with a second diameter, the first diameter of the extension wire being equal to the second diameter of the guide wire;
   (c) a hypotube having a proximal end, a distal end, an inner diameter and an outer diameter, the outer diameter of the hypotube being equal to the first diameter of the extension wire, the proximal end of the hypotube being permanently affixed to the distal end of the extension wire; and
   (d) a spring coil with a proximal end, a distal end, an inner diameter and an outer diameter, the outer diameter of the spring coil being equal to the outer diameter of the hypotube, the proximal end of the spring coil being axially aligned and permanently affixed to the distal end of the hypotube, the inner diameter of the spring coil being dimensioned to slidably fit the first diameter of the guide wire with a frictional fit such that when the first diameter of the guide wire is inserted into the distal end of the spring coil, the guide wire is held in place by frictional engagement with the spring coil.

4. The guide wire extension docking system of claim 3 wherein the guide wire, extension wire, hypotube and spring coil are made of stainless steel.

5. A method used in angoiplasty for docking an extension wire to a guide wire comprising the steps of:
   (a) providing a guide wire having a proximal end with a first diameter and a distal end with a second diameter, the first diameter being smaller than the second diameter;
   (b) providing an extension wire having a proximal end and a distal end,
   (c) providing a hypotube having a proximal end and a distal end, the hypotube being axially aligned with the extension wire, the proximal end of the hypotube being affixed to the distal end of the extension wire, the distal end of the hypotube having a tongue extending distally;
   (d) providing a spring coil having a proximal end, a distal end and an inner diameter, the spring coil being axially aligned with the hypotube and the spring coil being affixed to the tongue of the hypotube, the inner diameter of the spring coil being dimensioned to slidably fit the first diameter of the guide wire; and
   (e) inserting the proximal end of the guide wire into the distal end of the spring coil to releasably connect the guide wire and the extension wire together.

6. A method used in angoiplasty for docking an extension wire to a guide wire comprising the steps of:
   (a) providing a guide wire section having a proximal end with a first diameter and a distal end with a second diameter, the first diameter being smaller than the second diameter;
   (b) providing an extension wire having a proximal end and a distal end,
   (c) providing a hypotube having a proximal end and a distal end, the hypotube being axially aligned with the extension wire, the proximal end of the hypotube being affixed to the distal end of the extension wire;
   (d) providing a spring coil having a proximal end, a distal end and an inner diameter, the spring coil being axially aligned with the hypotube and the proximal end of the spring coil being affixed to the distal end of the hypotube, the inner diameter of the spring coil being dimensioned to slidably fit the first diameter of the guide wire; and
   (e) inserting the proximal end of the guide wire into the distal end of the spring coil to releasably connect the guide wire and the extension wire together.

* * * * *